US008076280B2

(12) United States Patent
Elder et al.

(10) Patent No.: US 8,076,280 B2
(45) Date of Patent: Dec. 13, 2011

(54) EMULSIONS CONTAINING ENCAPSULATED FRAGRANCES AND PERSONAL CARE COMPOSITIONS COMPRISING SAID EMULSIONS

(75) Inventors: Stewart T. Elder, Butler, NJ (US); Christina L. Andrianov, Hawthorne, NJ (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/998,957

(22) Filed: Dec. 3, 2007

(65) Prior Publication Data

US 2008/0153736 A1    Jun. 26, 2008

Related U.S. Application Data

(60) Provisional application No. 60/875,938, filed on Dec. 20, 2006.

(51) Int. Cl.
```
A61L 9/04      (2006.01)
C11D 3/50      (2006.01)
A61K 8/00      (2006.01)
A61K 8/02      (2006.01)
A61Q 1/14      (2006.01)
A61Q 19/00     (2006.01)
A61Q 19/10     (2006.01)
B01F 3/08      (2006.01)
C08L 83/00     (2006.01)
B01J 13/02     (2006.01)
```
(52) U.S. Cl. .............. 512/4; 510/119; 510/130; 516/28; 424/401; 523/201; 264/4.33
(58) Field of Classification Search ...... 512/4; 510/119, 510/130; 264/4.33; 424/642, 70.22, 401; 430/110.2; 516/28; 523/201; 525/902
See application file for complete search history.

(56) References Cited

U.S. PATENT DOCUMENTS

| | | | |
|---|---|---|---|
| 3,926,840 A * | 12/1975 | Wendler et al. .................. 516/28 |
| 4,464,271 A | 8/1984 | Munteanu et al. .............. 252/8.6 |
| 5,139,915 A * | 8/1992 | Moffat et al. ............... 430/110.2 |
| 5,185,395 A | 2/1993 | Robinson et al. .............. 524/457 |
| 5,382,567 A | 1/1995 | Fuwa et al. ......................... 512/4 |
| 5,804,538 A | 9/1998 | Wei et al. ....................... 510/101 |
| 5,804,632 A * | 9/1998 | Haddleton et al. ............. 524/458 |
| 5,891,833 A | 4/1999 | Wei et al. ....................... 510/121 |
| 6,024,952 A | 2/2000 | Story et al. ................... 424/78.03 |
| 6,039,900 A | 3/2000 | Symes et al. ..................... 264/4.1 |
| 6,048,520 A * | 4/2000 | Hoshowski ................. 424/70.17 |
| 6,194,375 B1 | 2/2001 | Ness et al. ......................... 512/4 |
| 6,225,372 B1 * | 5/2001 | Lykke et al. .................... 523/201 |
| 6,313,197 B1 * | 11/2001 | Symes et al. ................... 523/201 |
| 6,329,057 B1 | 12/2001 | Dungworth et al. ........... 428/403 |
| 6,359,031 B1 | 3/2002 | Lykke et al. .................... 523/201 |
| 6,375,983 B1 * | 4/2002 | Kantor et al. ................... 424/489 |
| 6,391,288 B1 | 5/2002 | Miyazawa et al. ............... 424/59 |
| 6,454,842 B1 | 9/2002 | Vernardakis et al. ....... 106/31.02 |
| 7,122,512 B2 | 10/2006 | Brain et al. ......................... 512/4 |
| 2003/0021847 A1 * | 1/2003 | Baxter et al. ................... 424/487 |
| 2003/0053976 A1 * | 3/2003 | Tournilhac et al. .......... 424/70.17 |
| 2003/0125222 A1 * | 7/2003 | Jahns et al. ..................... 510/130 |
| 2003/0133900 A1 * | 7/2003 | McLaughlin ............... 424/70.22 |
| 2003/0134910 A1 | 7/2003 | Rose et al. ....................... 516/53 |
| 2004/0071742 A1 * | 4/2004 | Popplewell et al. ........... 424/401 |
| 2004/0087477 A1 | 5/2004 | Ness ................................. 512/4 |
| 2004/0092414 A1 | 5/2004 | Clapp et al. .................... 510/130 |
| 2004/0234558 A1 | 11/2004 | O'Connor et al. ............. 424/401 |
| 2005/0227907 A1 * | 10/2005 | Lee et al. ........................... 512/4 |
| 2005/0276774 A1 * | 12/2005 | Elder et al. .................... 424/70.1 |
| 2006/0247323 A1 | 11/2006 | Rose et al. ....................... 516/73 |

FOREIGN PATENT DOCUMENTS

| | | |
|---|---|---|
| EP | 0925776 | 6/1999 |
| WO | 97/47288 | 12/1997 |
| WO | 99/21532 | 5/1999 |
| WO | 99/62477 | 12/1999 |
| WO | 00/41528 | 7/2000 |
| WO | WO 2005002719 A1 * | 1/2005 |
| WO | 2005/041918 | 5/2005 |

OTHER PUBLICATIONS

Verschoor et al Journal of Cleaner Production vol. 9 2001 pp. 277-286.*
Myristyl alcohol The Good Scents Company product data {http://www.thegoodscentscompany.com/data/rw1050721.html} circa 1980.*

* cited by examiner

Primary Examiner — James J Seidleck
Assistant Examiner — Aaron Greso
(74) Attorney, Agent, or Firm — Sheila A. Loggins; Tyler A. Stevenson

(57) ABSTRACT

The present invention provides an emulsion comprising an organic discontinuous phase which is distributed throughout a continuous aqueous phase,
wherein the organic phase comprises,
  a) an organic solvent which is a liquid at 25° C. and/or,
  b) an organic phase stabilising material that comprises hydrophobic moieties and is a material which is more soluble in the organic phase than the aqueous phase,
and the emulsion further comprises an encapsulated fragrance, said fragrance is encapsulated in microparticles.
The present invention also relates to personal care compositions comprising emulsions containing encapsulated fragrances for improved fragrance delivery.
The present invention also relates a method of use that comprises application of an effective amount of a liquid or solid personal care composition comprising an emulsion that contains a fragrance encapsulated in microparticles to at least one part of the body.

10 Claims, No Drawings

EMULSIONS CONTAINING ENCAPSULATED FRAGRANCES AND PERSONAL CARE COMPOSITIONS COMPRISING SAID EMULSIONS

This application claims benefit under 35 USC 119(e) of U.S. Provisional app. No. 60/875,938, filed on Dec. 20, 2006, which is incorporated herein by reference.

FIELD OF THE INVENTION

This invention relates to emulsions containing encapsulated fragrances for improved fragrance delivery in personal care compositions and personal care compositions comprising said emulsions.

BACKGROUND OF THE INVENTION

A general strategy currently employed for imparting odors to consumer products is admixing of the fragrance directly to the product. The major drawback of this procedure is that most of the fragrance is lost during manufacturing, storage, and use because the fragrance molecules are too volatile and/or too unstable. Often the fragrance is also lost because of lack of adhesion to the support to be perfumed, e.g. skin, hair, fabric, tile, or any other surface.

It is frequently desirable or advantageous to treat the surfaces of a variety of substrates, for example skin or hair, with benefit agents such as perfumes, flavors, pharmaceuticals and/or biocontrol agents including biocides, insecticides, mildewcides, and the like. The objective of such treatment is generally to leave deposited on the surfaces of the substrates enough benefit agent so that there is a residual benefit imparted to the substrate surface.

In many consumer products, it is desirable for perfume, especially perfume raw materials to be released slowly over time. Since the more volatile perfume raw materials are responsible for the "fresh feeling" that consumers experience, it is desirable for the more volatile perfume raw materials to be released in a slow, controlled manner.

In some cases, the fragrances are treated with cyclodextrins to form inclusion complexes which decrease the volatility and improve stability. However, these methods give often unsatisfactory results or are too expensive. For example, as described in U.S. Pat. No. 5,382,567, a major drawback of the heretofore used cyclodextrins is their high water solubility as soon as they are used in aqueous applications, said disclosure is herein incorporated by reference.

WO 2000/41528 discloses a controlled release composition comprising an adsorbent polymer, an active agent, and a release retardant.

U.S. Pat. No. 6,024,952 discloses a personal washing formulation containing a cationic polymer and an anionic emollient and said disclosure is incorporated herein by reference.

EP 925,776 discloses a polymer presenting binding sites for at least one organoleptic substance.

U.S. Pat. No. 6,329,057 discloses polymer particles comprising a hydrophobic organic matrix and, located at the exterior, free cationic groups and said disclosure is incorporated herein by reference.

U.S. Pat. No. 6,194,375 discloses organic polymer particles which have a further polymer at their exterior and an absorbed perfume and said disclosure is incorporated herein by reference.

WO 99/62477 discloses a method for cleansing and providing an increased fragrance benefit after rinsing the skin.

WO 99/21532 discloses a personal care cleansing and conditioning product that contains a fragrance.

WO 97/48378 discloses a process for preparing liquid personal cleansing composition which contains a fragrance.

WO 2005/041918 discloses a fragrance delivery system consisting of a mixture of polymer oligomers and stabilizers.

U.S. Pat. No. 6,454,842 discloses a scented ink composition and method of preparation and said disclosure is incorporated herein by reference.

US 2003/0134910 and WO 2002/00023 disclose an emulsion comprising an organic discontinuous phase which is distributed through a continuous aqueous phase, and which is useful for protecting light sensitive pesticides.

US 2004/0092414 discloses rinse-off personal care compositions comprising a perfume polymeric particle perfume raw material delivery system.

WO 1997/48374 discloses liquid personal cleansing compositions.

US 2004/0234558 discloses personal product compositions comprising benefit agent premix or delivery vehicles.

EP 1,407,753 discloses a polymeric encapsulated fragrance wherein the polymer encapsulated shell is coated with a polyamine polymer.

Accordingly, there is a need for an emulsion comprising an encapsulated fragrance which enhances/increases the level of perfume raw materials that deposit onto and/or release from a substrate and methods for delivering perfume raw materials to a substrate, particularly skin and/or hair.

SUMMARY OF THE INVENTION

The present invention provides an emulsion comprising an organic discontinuous phase which is distributed throughout a continuous aqueous phase,
wherein the organic phase comprises,
 a) an organic solvent which is a liquid at 25° C. and/or,
 b) an organic phase stabilising material that comprises hydrophobic moieties and is a material which is more soluble in the organic phase than the aqueous phase,
and the emulsion further comprises an encapsulated fragrance, said fragrance is encapsulated in microparticles.

This invention also relates to personal care compositions comprising emulsions containing encapsulated fragrances for improved fragrance delivery.

The present invention also relates to a method of use that comprises application of an effective amount of a liquid or solid personal care composition comprising an emulsion that contains a fragrance encapsulated in microparticles to at least one part of the body.

DETAILED DESCRIPTION OF THE INVENTION

The present invention provides an emulsion comprising an organic discontinuous phase which is distributed throughout a continuous aqueous phase,
wherein the organic phase comprises,
 a) an organic solvent which is a liquid at 25° C. and/or,
 b) an organic phase stabilising material that comprises hydrophobic moieties and is a material which is more soluble in the organic phase than the aqueous phase,
and the emulsion further comprises an encapsulated fragrance, said fragrance is encapsulated in microparticles.

The organic phase may comprise any organic solvent that is a liquid at 25° C. and is a substance in which the fragrance or perfume raw material active is soluble, miscible or dispersible. For example, the fragrance active is dissolved in the organic solvent. The organic solvent may be an aromatic or aliphatic organic liquid, for instance a $C_3$ or greater alkyl substituted aromatic compound or an alkyl benzene/solvent naphtha. For instance, the organic solvent is an alkyl ester of a carboxylic acid. For example, the solvent is a carboxylic acid ester in which the alcohol moiety contains at least 4 carbon atoms, for instance a C4-30 alkyl ester of a carboxylic acid. Typically, this may be a monomeric but saturated ester such as isobutyl acetate, lauryl acetate, isobutyl isobutyrate and lauryl isobutyrate. It may, for instance, be a monomeric ethylenically unsaturated ester, for instance isobutyl methacrylate or lauryl methacrylate.

When the organic phase comprises an organic solvent it is ideally present in an amount that promotes both stability of the emulsion and longevity of the fragrance active. Typically, the organic solvent is used in an amount from about 0.01% to about 50% by weight based on the total weight of the emulsion. For example, the emulsion comprises the organic solvent in an amount from about 0.1% to about 40% by weight, for instance from about 1% to about 30% by weight. For instance, highly effective results are obtained when the emulsion comprises from about 1% to about 10% by weight organic solvent.

Alternatively, the organic phase comprises an organic phase stabilising material that is a substance which is more soluble in the organic phase in comparison to the aqueous continuous phase. The organic phase stabiliser may be selected from addition copolymers formed from a) at least one ethylenically unsaturated monomer containing $C_{8-30}$ alkyl moieties, b) at least one ethylenically unsaturated carboxylic acids or ethylenically unsaturated acid anhydrides and c) optionally other water insoluble ethylenically unsaturated monomers. The ethylenically unsaturated monomer containing $C_{8-30}$ alkyl moieties may be for instance (meth)acrylic esters, N-substituted (meth)acrylamides and (meth)allyl ethers. For example, the organic phase stabilising material is selected from addition polymers formed from a monomer mixture comprising a) from about 40 to about 90% by weight $C_{8-30}$ alkyl (meth)acrylate, b) from about 10 to about 40% by weight of at least on monomer selected from the group consisting of maleic acid, maleic anhydride, acrylic acid and methacrylic acid and c) 0 to about 50% by weight at least one monomer selected from the group consisting of $C_{1-7}$ alkyl (meth)acrylates, styrene, vinyl acetate and acrylonitrile.

In another embodiment of the instant invention, the organic phase stabilising material is a copolymer of stearyl methacrylate/maleic anhydride/styrene.

In another embodiment of the instant invention, the organic phase stabilising material is a copolymer of stearyl methacrylate/maleic anhydride/styrene wherein the monomer weight ratio is 60/10/30, based on monomer weight.

Typically, the polymeric organic phase stabilisers may be prepared by polymerising the monomer mixture in an organic solvent using standard polymerisation techniques. Such polymers may suitably be formed by polymerisation of a solution of the monomer blend in a suitable organic solvent and for instance employing suitable radical generating initiators, for instance thermal initiators e.g. azobisiosbutyronitrile (AZDN).

For example, an alternative organic phase stabiliser is a low hydrophilic/lipophilic balance (HLB) surfactant. Typically the surfactant comprises a hydrophilic/lipophilic balance of below 7, preferably in the range 2 to 6. The low HLB surfactant may not necessarily be a polymer, provided that the compound comprises hydrophilic and lipophilic moieties in proportions such that it is more soluble in the organic phase that the aqueous phase. For example, a low HLB surfactant according to the invention includes sorbitan monooleate.

The amount of organic phase stabilising material required will vary depending upon the particular stabiliser and the proportion of dispersed phase to aqueous phase contained in the emulsion. Generally in order to achieve maximum stability and protection for the fragrance, it is desirable for the organic phase stabilising material to be present in the emulsion in an amount from about 0.01 to about 15.0% by weight of the emulsion. However, good results are also obtained when the stabiliser is present in an amount from about 1.5 to about 8% based on the total weight of the emulsion.

For instance, the emulsion comprises in the organic phase both an organic solvent in an amount of from about 5 to about 50% by weight and an organic phase polymeric stabiliser in an amount of from about 0.1 to about 15.0% by weight, both based on the total weight of the emulsion.

It may be desirable to include other ingredients in the encapsulated fragrance emulsion of the first aspect of the invention. For instance in order to prevent problems with instability when exposed to cold temperatures, it may be desirable to include antifreeze additives, for instance monopropylene glycol and monoethylene glycol.

For example, in another embodiment of the invention an encapsulated fragrance formulation comprising a stable emulsion which comprises an organic phase which contains i) an encapsulated fragrance and ii) an organic solvent which is liquid at 25° C. and/or an organic phase stabilising material comprises hydrophobic moieties and is a material which is more soluble in the organic phase than the aqueous phase, said organic phase being distributed throughout an aqueous continuous phase that contains water and a water-soluble stabilising material which is a water-soluble stabilising polymer which has a plurality of hydrophilic and hydrophobic groups and optionally an antifreeze compound.

In another embodiment of the invention, the fragrance is encapsulated in microparticles. The microparticles consist of a core-shell configuration. It is preferred that the particles have a core-shell configuration in which the core comprises a polymeric particle surrounded by a polymeric shell. More preferably, the particles comprise a core comprising the polymeric particle and a shell comprising the water-soluble or partially water-soluble polymer. It is particularly preferable that the shell of the water-soluble or partially water-soluble polymer is formed around the core of polymeric particle during polymerization.

The core polymer or copolymer is formed from the combination of methacrylate or acrylate monomers and vinyl monomers are capable of forming a copolymer of glass transition temperature (Tg) below 50° C., preferably below 40° C.

The glass transition temperature (Tg) for a polymer is defined in the Encyclopedia of Chemical Technology, Volume 19, fourth edition, page 891, as the temperature below which (1) the transitional motion of entire molecules and (2) the coiling and uncoiling of 40 to 50 carbon atom segments of chains are both frozen. Thus, below its Tg a polymer would not exhibit flow or rubber elasticity.

The Tg of a polymer may be determined using Differential Scanning Calorimetry (DSC).

For the purposes of the invention, all styrene based copolymers with alkyl(meth)acrylates giving a Tg of less than 50° C., preferably less than 40° C. can be used as the styrene-acrylate core polymer or copolymer.

The (meth)acrylate monomers used to form the core polymer or copolymer are for example selected from the group consisting of n-butyl (meth)acrylate, 2-ethylhexyl (meth) acrylate, hexyl (meth)acrylate, isopropyl (meth)acrylate, decyl or lauryl (meth)acrylate, t-butyl (meth)acrylate, isobutyl(meth)acrylate, ethyl (meth)acrylate, glycidyl (meth)acrylate, hydroxyalkyl (meth) acrylates and dicarboxylic ester monomers such as maleates and propyl (meth)acrylate. The preferred (meth)acrylate monomers are n-butyl (meth)acrylate, 2-ethylhexyl (meth)acrylate and t-butyl (meth)acrylate or mixtures thereof.

The vinyl polymerizable monomer or monomers of the core polymer or copolymer are selected from the group consisting of methyl (meth)acrylate, isobutyl (meth)acrylate, styrene, and styrene derivatives such as α-methyl styrene, alkylated styrene and mixtures thereof. The preferred vinyl polymerizable monomer or monomers are methyl methacrylate, styrene or alkylated styrene.

The vinyl polymerizable monomer for the core polymer or copolymer is a monomer such as those described above which do not contain an acid functionality such as (meth)acrylic acid or acrylic acid. In particular, styrene, α-methyl styrene and alkylated styrene are preferred.

The weight ratio of the (meth)acrylate monomers to vinyl polymerizable monomers in the core polymer or copolymer ranges from about 30/70 to about 70/30, preferably the weight ratio of (meth)acrylate monomers to vinyl polymerizable monomers is about 35/60 to about 60/35. Most preferably, the weight ratio is about 40/60 to about 60/40 based on the total weight of the core polymer or copolymer.

For example, the core polymers or copolymers of the invention include:
50 weight % n-butylacrylate and 50 weight % styrene,
45 weight % n-butyl acrylate and 55 weight % styrene,
40 weight % 2-ethylhexyl acrylate and 60 weight % styrene,
40 weight % 2-ethylhexyl acrylate and 30 weight % methyl methacrylate and 30 weight % styrene, and
45% weight % 2-ethylhexyl acrylate and 55% weight % styrene.

Each of these examples gives a low Tg (under 50° C.). For example, a 55/45 styrene 2-ethylhexyl acrylate core copolymer gives a Tg of about 22° C.

The average molecular weight for the core polymer or copolymer ranges from about 150,000 to about 350,000 g/mol (determined by GPC using standard industrial parameters). Preferably the polymer has a molecular weight of from about 200,000 to about 300,000 g/mol. More preferably the optimum molecular weight for the matrix polymer is from about 200,000 to about 275,000 g/mol.

Generally the average particle size diameter of the core polymer or copolymer is less than about 300 nanometers. For example, the average particle size diameter is in the range of about 60 to about 200 nanometers; for instance, from about 60 to about 150 nanometers. Average particle size is determined by a Coulter particle size analyzer according to standard procedures well documented in the literature.

In order to obtain an aqueous dispersion from these vinyl monomers, it suffices to perform an emulsion polymerization of the monomers by well-known methods to produce a stable dispersion using hydrophilic catalysts, such as ammonium persulfate, potassium persulfate or aqueous hydrogen peroxide, or redox catalysts.

The shell polymer or copolymer present during the polymerization of the core polymer or copolymer is made by co-polymerizing (meth)acrylic acid or acrylic acid, and a vinyl polymerizable monomer other than an acid monomer to form a copolymer of a glass transition temperature (Tg) that ranges from about 50° C. to about 120° C., preferably from about 70° C. to about 120° C. and most preferably the Tg ranges from about 80° C. to about 110° C.

The vinyl polymerizable monomer or monomers of the shell polymer or copolymer contain (meth)acrylic acid or acrylic acid and a vinyl monomer other than the acid monomer. At least one of the vinyl monomers is preferably selected from the group consisting of styrene, alkylated styrene, α-methyl styrene, butyl (meth)acrylate, methyl (meth)acrylate and mixtures thereof.

The shell polymer or copolymer is an acid containing polymer made by copolymerizing (meth)acrylic acid or acrylic acid, and a vinyl polymerizable monomer other than the (meth)acrylic acid or acrylic acid and is formed from about 10 to about 50 weight % acrylic acid, methacrylic acid or mixtures, preferably about 10 to about 45 weight % and about 90 to about 50 weight % of a vinyl polymerizable monomer other than the (meth)acrylic acid or acrylic acid monomer, preferably from about 90 to about 55 weight %. The monomer percentages are based on total weight of the polymer or copolymer.

Examples of appropriate shell polymers or copolymers are:
65% styrene and 35% acrylic acid;
43% isobutyl methacrylate, 43% methyl methacrylate and 14% acrylic acid;
43% butyl acrylate, 43% methyl methacrylate and 14% acrylic acid; and
80% ethylene and 20% acrylic acid.

The salts of the shell polymer or copolymer may be any salt as long as the polymer maintains the emulsifying properties. Preferably, the polymer or copolymer contains a volatile salt; for example, an ammonium salt.

The shell polymer or copolymer has an average molecular weight of about 6,000 to about 15,000 g/mol. Preferably the shell polymer has an average molecular weight of about 6,000 to about 12,000 g/mol. Most preferably, the shell polymer has an average molecular weight of about 6,000 to about 10,000 g/mol.

The core-shell polymer or copolymer is provided in an aqueous emulsion and may include other additives such as thickening agents, defoaming or antifoaming agents, pigments, slip additives, release agents, fluorochemicals, starches, waxes and antiblocking agents. Components such as fluorochemicals, starches and waxes can also be added to improve oil, grease and other barrier properties such as water repellency and water vapor transmission barrier.

Generally the average particle size diameter of the microparticles is from about 100 nanometers to about 100 micrometers. For example, the average particle size diameter is in the range of about 500 nanometers to about 50 micrometers; for instance, from about 1 micrometer to about 25 micrometers. Average particle size is determined by a Coulter particle size analyzer according to standard procedures well documented in the literature.

When the emulsion is for instance a fragrance concentrate containing for instance at least 10% perfume raw materials, it may be used as such directly or alternatively diluted. Typically the concentrate would be diluted to an active concentration of about 0.1 to about 0.5% by weight perfume raw material.

As used herein, the term "fragrance" can include perfume or perfume ingredients or raw materials, cooling agents and other tactile agents, or combinations thereof.

The encapsulated fragrance comprised within the instant emulsion comprises from about 0.001% to about 90% by weight based on the total weight of the emulsion; for example, from about 40% to about 80%; for instance, from about 50% to about 70% weight based on the total weight of the emulsion.

The fragrance which is encapsulated comprises from about 0.001% to about 20% weight based on the total weight of the emulsion; for example, from about 0.01% to about 10%; for instance, from about 0.1% to about 1% weight based on total weight of the emulsion.

The fragrance or perfume ingredients employed in the emulsions of the present invention are the conventional ones known in the art. Even perfume ingredients which are unstable due to volatility (as exhibited by changes in intensity) or discoloration when used in their neat form are stable and suitable for use in the emulsions of the present invention when they are impregnated in a fragrance carrier as hereinafter described. As used herein, a fragrance is considered to be "stale" if the fragrance does not exhibit appreciable changes in color or intensity and does not exhibit appreciable loss due to volatility after 10 days at 120 degrees F.

Suitable perfume compounds and compositions can be found in the art including U.S. Pat. Nos. 4,145,184, Brain and Cummins, issued Mar. 20, 1979; 4,209,417, Whyte, issued Jun. 24, 1980; 4,515,705, Moeddel, issued May 7, 1985; 4,152,272, Young, issued May 1, 1979; 5,378,468 Suffis et al., U.S. Pat. No. 5,081,000 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/38528 published Dec. 5, 1996; "WO 96/14827 published May 23, 1996; WO 95/04809 published Feb. 16, 1995; and WO 95/16660 published Jun. 22, 1995; all of said U.S. patents and U.S. references being incorporated herein by reference. In addition P. M. Muller, D Lamparsky *Perfumes Art, Science, & Technology* Blackie Academic & Professional, (New York, 1994) is included herein by reference.

Perfumes can be classified according to their volatility. The highly volatile, low boiling, perfume ingredients typically have boiling points of about 250 degrees C. or lower. The moderately volatile perfume ingredients are those having boiling of from about 250 degrees C. to about 300 degrees C. The less volatile, high boiling, perfume ingredients are those having boiling points of about 300 degrees C. or higher. Many of the perfume ingredients as discussed hereinafter along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, lnalool, linalool oxide, linalyl acetate, linalyl propionate, methyl anthranilate, alpha-methyl ionone, methyl nonyl acetaldehyde, methyl phenyl carbonyl acetate, laevo-menthyl acetate, menthone, iso-menthone, myrcene, lyrcenyl acetate, myrcenol, mero, meryl acetate, nonyl acetate, phenyl ethyl alcohol, alpha-pinene, beta-pinene, gamma phenene, alpha-terpineol, beta-terpineol, terpinyl acetate, and vertenex (para-tertiary-butyl cyclohexyl acetate). For example, lavadin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbonyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, merolidol, patchouli alcohol, phenyl hexanol, geta-selinene, trichloromethyl phenyl carbonyl acetate, triethyl citrate, vanillin, and veratraldehyde. Cedar terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gamma-2-benzopyran), hexyl cinnamic aldehyde, lyral (4-(4-hydroxy-4-methyl pentyl)-3-cyclohexene-10-caroxaldehyde), methyl cedrylone, methyl dihydro jasmonate, methyl-beta-napthyl ketone, musk indanone, musk ketone, musk tibetene, and phenylethyl phenyl acetate.

As hereinbefore indicated, the fragrance employed in the present invention can also comprise a cooling agent or a combination of cooling agents. Cooling agents are compounds which directly effect those nerve endings responsible for hot or cold sensations. Suitable cooling agents are menthol, menthol-based or acyclic carboximides, camphor, Eucalyptus, and menthol-based or acyclic ketals (acetals). For example, the cooling agents for use in the present invention are those selected from the group consisting of 3-1-menthoxy propane-1,2-diol, N-substituted-p-menthane-3-carboxamides and acyclic carboxamides and mixtures thereof.

3-1-menthoxy propane 1,2-diol is fully described in detail in U.S. Pat. No. 4,459,425, issued Jul. 10, 1984 to Amano et. al., incorporated herein by reference in its entirety. This volatile aromatic is commercially available, as TJ-10 from Takasago Perfumery Co., LTD., Tokyo, Japan.

The N-substituted-p-menthatne-3-carboxamides are fully described in U.S. Pat. No. 4,136,163 to Watson et al., issued Jan. 23, 1979 incorporated herein by reference in its entirety. For example, a cooling agent of this class is N-ethyl-p-menthane-3-caboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. For example, a cooling agent of this class is N,-2,3-trimethyl-2isoproylbutanamide in a ratio of 1:75:42, respectively.

Another embodiment of the instant invention is a personal care composition comprising an emulsion comprising an organic discontinuous phase which is distributed throughout a continuous aqueous phase,
wherein the organic phase comprises,
  a) an organic solvent which is a liquid at 25° C. and/or,
  b) an organic phase stabilising material that comprises hydrophobic moieties and is a material which is more soluble in the organic phase than the aqueous phase,
and the emulsion further comprises an encapsulated fragrance, said fragrance is encapsulated in microparticles.

The personal care composition according to the invention comprises from about 0.01 to about 40% by weight of the emulsion based on the total weight of the personal care composition; for example, from about 1 to about 20% by weight; and, for instance, from about 2 to about 15% by weight.

The personal care composition may contain other ingredients as well; for example, a cosmetically tolerable carrier or adjuvant and, optionally, adjunct ingredients. While water is cosmetically tolerable, and in most instances will also be present, the phrase "a cosmetically tolerable carrier or adjuvant" is intended to refer to at least one substance other than water that is customarily employed in personal care or cosmetic compositions.

"Adjunct ingredients" as used herein means those ingredients that are used in the process for preparing the benefit agent polymeric delivery system. For example, such a delivery system includes personal care/cleansing products, hair products and the like. Adjunct ingredients are also referred to as product formulation ingredients.

Personal care compositions according to the invention may be contained in a wide variety of personal care preparations. Especially the following preparations, for example, come into consideration:

shaving preparations, e.g. shaving soap, foaming shaving creams, non-foaming shaving creams, foams and gels, preshave preparations for dry shaving, aftershaves or aftershave lotions;

skin-care preparations, e.g. skin emulsions, multi-emulsions or skin oils and body powders;

cosmetic personal care preparations, e.g. facial make-up in the form of lipsticks, eye shadow, eye liners, liquid make-up, day creams or powders, facial lotions, foundations, creams and powders (loose or pressed);

light-protective preparations, such as sun tan lotions, creams and oils, sun blocks and pretanning preparations;

manicure preparations, e.g. nail polishes, nail enamels, enamel removers, nail treatments deodorants, e.g. deodorant sprays, pump-action sprays, deodorant gels, sticks or roll-ons;

antiperspirants, such as antiperspirant sticks, creams or roll-ons; and solid/liquid personal cleaning products, such as soap, cleansers, shampoo, conditioners, hair treatments.

Another embodiment of the instant invention is a personal care composition which is formulated as a water-in-oil or oil-in-water emulsion, as an alcoholic or alcohol-containing formulation, as a vesicular dispersion of an ionic or non-ionic amphiphilic lipid, as a gel, or a solid stick as an aqueous or non-aqueous system.

Another embodiment of the instant invention is a personal care composition which further comprises at least one further constituent selected from the group consisting of sequestering agents, non-encapsulated colorings, perfumes, thickening or solidifying (consistency regulator) agents, emollients, UV absorbers, surfactants, bleaching agents, skin-protective agents, antioxidants and preservatives.

The personal care compositions of the present invention may contain one or more additional skin care, nail care, or hair care components. In a preferred embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The CTFA Cosmetic Ingredient Handbook, Second Edition (1992) describes a wide variety of non-limiting cosmetic and pharmaceutical ingredients commonly used in the personal care industry, which are suitable for use in the personal care compositions of the present invention.

The present invention may optionally comprise an oil structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec-1, preferably 200 to about 100,000 poise, and most preferably 200 to about 50,000 poise. The amount of structurant required to produce this viscosity will vary depending on the oil and the structurant, but in general, the structurant will preferably be less than 75 weight percent of the dispersed oil phase, more preferably less than 50 weight percent, and still more preferably less than 35 weight percent of the dispersed oil phase.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001; herein incorporated by reference.

Non-limiting examples of anionic surfactants useful in the personal care compositions of the present invention are disclosed in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al., issued Dec. 30, 1975; herein incorporated by reference.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-limiting examples of nonionic surfactants for use in the personal care compositions of the present invention are disclosed in McCutcheon's, Detergents and Emulsifiers, North American edition (1986), published by Allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected from the group consisting of C8-C14 glucose amides, C8-C14 alkyl polyglucosides, sucrose cocoate, sucrose laurate, lauramine oxide, cocoamine oxide and mixtures thereof.

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the personal care compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by Allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, C.sub.12-14 glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

A wide variety of non-lathering surfactants are useful herein. The personal care compositions of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

In addition, there are several commercial emulsifier mixtures that are useful in some embodiments of the personal care compositions according to the present invention. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)-N—N-Dimethyl, N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse.

The personal care compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the Stability Agent is to say that it must build viscosity in the product. This can be measured using the Stability Agent Viscosity Test. Preferably, the stability agent produces a viscosity in this test of at least 1000 cps, more preferably at least 1500 cps, and still more preferably at least 2000 cps.

Nonlimiting examples of thickening agents useful herein include carboxylic acid polymers such as the carbomers (such as those commercially available under the trade name CARBOPOL® 900 series from B.F. Goodrich; e.g., CARBOPOL® 954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the cross linking agent is an allyl ether of sucrose or pentaerytritol. These copolymers are known as acrylates/$C_{10-30}$ alkyl acrylate crosspolymers and are commercially available as CARBOPOL® 1342, CARBOPOL® (1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein is the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the trade name NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another nonlimiting class of thickening agents useful herein is the gums. Nonlimiting examples of gums useful herein include hectorite, hydrated silica, xantham gum, and mixtures thereof.

Yet another nonlimiting class of thickening agents useful herein is the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth—25 Methacrylate Crosspolymer) from Clariant and cationic stabylens.

The personal care compositions according to the present invention may also contain organic cationic deposition polymers. Concentrations of the cationic deposition polymers preferably range from about 0.025% to about 3%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Nonlimiting examples of cationic deposition polymers for use in the personal care compositions include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquatemium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the personal cleansing composition herein are water soluble or dispersible, non cross linked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the personal care compositions ranges from about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

Personal care compositions according to the invention may be prepared by physically blending suitable emulsions comprising encapsulated fragrances into personal care compositions or formulations by methods which are well known in the art. The examples illustrate several of such methods.

In one embodiment of the method, the personal care or cosmetic composition comprises a blend of encapsulated fragrances that are individually provided in a single polymeric matrix material. In another, the personal care or cosmetic composition comprises a blend of microparticles as described above containing different encapsulated fragrances that are individually provided in separate polymeric matrix materials.

Another embodiment of the present invention is a method for caring/cleansing the hair and skin comprising the steps of:
a) wetting the hair and/or skin with water,
b) applying an effective amount of a personal care composition comprising an emulsion comprising an encapsulated fragrance to the hair and/or skin, and
c) rinsing the composition from the hair and/or skin using water.

These steps can be repeated as many times as desired to achieve the desired personal care and fragrance deposition benefits.

Another embodiment of the instant invention is a method of improved fragrance delivery to the human body said method comprising the steps of:
a) applying an effective amount of a personal care composition comprising an emulsion containing an encapsulated fragrance to at least one part of the human body; and
b) rubbing the effected part of the human body with sufficient force to efficiently distribute the personal care composition evenly.

It should be understood that compositions according to the present invention may contain additional polymers as adjunct ingredients separate from the microparticles that may be pre-mixed with the perfume polymeric particles and/or polymeric particles.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

Example 1

Preparation of an Emulsion Containing an Encapsulated Fragrance

The oil phase is prepared by adding 10.0 parts of a floral fragrance (Moonlight Path, IFF), 5.0 parts of a cosmetic oil Finsolv TN (C12-15 alkyl benzoate, Fintex), and 2.0 parts of oil soluble stabilizer copolymer of stearyl methacrylate, styrene and maleic anhydride (60/30/10% by weight) to a 25 ml beaker. The mixture is stirred until a homogeneous solution is obtained. In a separate 150 ml beaker, the aqueous phase is prepared by adding 60.0 parts deionized water (DI), 7.0 parts propylene glycol, and 11.0 parts of the emulsion copolymer prepared in Example 8. The mixture is stirred with a Silverson homogenizer at a low speed until all components are dissolved. The homogenizer speed is increased as the oil phase is slowly added. The resulting emulsion with encapsulated fragrance is homogenized at a speed to achieve particles of 1-5 microns in diameter.

Example 2

Preparation of a Conditioning Shampoo an Emulsion Containing an Encapsulated Fragrance A conditioning shampoo containing the encapsulated fragrance is prepared with the following composition:

|  | Trade name | INCI-Name | Supplier | Composition A % w/w (as supplied) | B % w/w (as supplied) |
|---|---|---|---|---|---|
| Part A | DI Water | Water |  | 48.45 | 44.65 |
| Part B | SALCARE Super 7 | Polyquaternium-7 | Ciba | 1.00 | 1.00 |
| Part C | Jeemide CME | Cocamide MEA | Jeen | 3.00 | 3.00 |
|  | Procetyl AWS | PPG-5 Ceteth 20 | Croda | 2.75 | 2.75 |
|  | Lipocol O-20 | Oleth-20 | Lipo | 1.00 | 1.00 |
|  | Glycol Distearate | Glycol Distearate | Lipo | 2.50 | 2.50 |
| Part D | Jeelate ES-1 | Sodium Laureth Sulfate | Jeen | 25.00 | 25.00 |
|  | Plantaren 2000N | Decyl Glucoside | Cognis | 15.00 | 15.00 |
| Part E | Liquid Germall ® Plus | Propylene Glycol (and) Diazolidinyl Urea (and) | ISP | 0.50 | 0.50 |

-continued

| | Trade name | INCI-Name | Supplier | Composition A % w/w (as supplied) | Composition B % w/w (as supplied) |
|---|---|---|---|---|---|
| Part F | DL-Panthenol 50W | Iodopropynyl Butylcarbamate Panthenol | BASF | 0.30 | 0.30 |
| Part G | Fragrance Moonlight Path Encapsulated Moonlight Path (11.6% fragrance, Example 1) | Fragrance | IFF Ciba | 0.50 — | — 4.30 |

In an appropriate vessel, Part A is added and moderate agitation is started. Part B is added and the mixture is heated to 70° C. The ingredients under Part C are added with mixing between each addition. The mixture is mixed for 20 minutes and then allowed to cool. The ingredients under Part D are added and mixed until homogeneous. The mixture is allowed to cool to 50° C. Part E is added, mixed for 15 minutes, and allowed to cool to 35° C. The ingredients under Part F are added with mixing in between. The fragrances in Part G are added and mixed well. The batch is then allowed to cool to room temperature.

Example 3

Evaluation of the Shampoo on Hair Tresses

Hair tresses are treated with 2 ml of the formulation in Instant Example 2 and rubbed in for 1 minute. The tresses are then rinsed with water for 30 seconds. The hair tresses are allowed to air dry.

Each panelist is allowed to sniff the coded hair tress and is asked to determine whether or not a stronger fragrance can be detected for each hair tress or if no difference could be determined. The results are shown in the table below.

Panel Results:
Sensory test of hair tress treated with conditioning shampoo containing either encapsulated fragrance vs. control.
Hair tresses are evaluated blind. The individual commented on which hair tress has the stronger fragrance.

| Individual | A (Control) | B (encapsulated Fragrance) |
|---|---|---|
| #1 | weaker | stronger |
| #2 | weaker | stronger |
| #3 | weaker | stronger |
| #4 | No difference | No difference. |
| #5 | weaker | stronger |
| #6 | No difference. | No difference |

This demonstrates that hair treated with the instant invention retains a stronger fragrance than hair treated with a conditioning shampoo without the encapsulated fragrance.

Example 4

Preparation of an Emulsion Containing an Encapsulated Fragrance

The procedure of Example 1 is repeated with an evergreen fragrance. An emulsion containing an encapsulated fragrance is obtained.

Example 5

Preparation of an Emulsion Containing an Encapsulated Vanilla Fragrance

The oil phase is prepared by adding 5.0 parts of vanilla (Carrubba), 2.5 parts of a cosmetic oil Finsolv TN (C12-15 alkyl benzoate, Fintex), and 2.0 parts of oil soluble stabilizer (sorbitan monooleate, Span 80) to a 25 ml beaker. The mixture is stirred until a homogeneous solution is obtained. In a separate 100 ml beaker, the aqueous phase is prepared by adding 35.0 parts DI water, 3.75 parts butylene glycol, and 7.0 parts of the emulsion copolymer obtained in Instant Example 8. The mixture is stirred with a Silverson homogenizer at a low speed until all components are dissolved. The homogenizer speed is increased as the oil phase is slowly added. The resulting emulsion is homogenized at a speed to achieve particles of 1-5 microns in diameter.

Example 6

Preparation of an Emulsion Containing an Encapsulated Mango Fragrance

The oil phase is prepared by adding 5.0 parts of a mango oil fragrance (Mango Oil, Carrubba), 2.5 parts of a cosmetic oil Finsolv TN (C12-15 alkyl benzoate, Fintex), and 2.0 parts of oil soluble stabilizer (sorbitan monooleate, Span 80) to a 25 ml beaker. The mixture is stirred until a homogeneous solution is obtained. In a separate 100 ml beaker, the aqueous phase is prepared by adding 35.0 parts DI water, 3.75 parts butylene glycol, and 7.0 of the emulsion copolymer obtained in Instant Example 8. The mixture is stirred with a Silverson homogenizer at a low speed until all components are dissolved. The homogenizer speed is increased as the oil phase is slowly added. The resulting emulsion is homogenized at a speed to achieve particles of 1-5 microns in diameter.

Example 7

Preparation of an Emulsion Containing an Encapsulated Orange

The oil phase is prepared by adding 5.0 parts of an orange oil (Orange Oil, IFF), 2.5 parts of a cosmetic oil Finsolv TN (C12-15 alkyl benzoate, Fintex), and 2.0 parts of oil soluble stabilizer (sorbitan monooleate, Span 80) to a 25 ml beaker. The mixture is stirred until a homogeneous solution is obtained. In a separate 100 ml beaker, the aqueous phase is prepared by adding 35.0 parts DI water, 3.75 parts butylene glycol, and 7.0 parts of a copolymer consisting of butyl acrylate, ethyl acrylate, methyl methacrylate and methacrylic acid (30/30/25/15% by weight, aqueous stabilizer). The mixture is stirred with a Silverson homogenizer at a low speed until all components are dissolved. The homogenizer speed is increased as the oil phase is slowly added. The resulting emulsion is homogenized at a speed to achieve particles of 1-5 microns in diameter.

Stability is based on whether or not the emulsion significantly looses the fragrance after one week in storage at the conditions listed below as judged by a human stiff test for fragrance intensity.

Composition and Stability of Encapsulated Orange Oil Fragrance

Stability of the resulting product was determined after 1 week at 45° C.

| | Oil Phase | | | Aqueous Phase | | | | |
|---|---|---|---|---|---|---|---|---|
| RUN | Fragrance (g) | Solvent (g) | Org. Stab (g) | Aq. Stab (g) | PG (g) | Water (g) | TOTAL (g) | Stability |
| A | 5.00 | 2.50 | 0.50 | 7.00 | 3.75 | 35.0 | 50.00 | No |
| B | 5.00 | 2.50 | 1.50 | 7.00 | 3.75 | 35.0 | 50.00 | No |
| C | 5.00 | 2.50 | 1.00 | 6.00 | 3.75 | 35.0 | 50.00 | No |
| D | 5.00 | 2.50 | 0.50 | 5.00 | 3.75 | 35.0 | 50.00 | No |
| E | 5.00 | 2.50 | 1.50 | 5.00 | 3.75 | 35.0 | 50.00 | No |

Org. Stab. is oil soluble stabilizer;
Aq. Stab. is aqueous stabilizer;
PG is propylene glycol.

This demonstrates that non-encapsulation of the fragrance leads to unstable fragrance compositions or emulsions.

Example 8

Preparation of a Core Shell Copolymer

To a laboratory reactor equipped with the necessary auxiliary equipment is added a styrene/acrylic acid copolymer as the ammonium salt (65 wt % styrene/35 wt % acrylic acid as the ammonium salt, 988 g, molecular weight is 7,000), water (3520 g), ammonium persulfate (3.4 g), and Tetralon B (1.5 g). The stirred reactor contents are heated to 85 C. The monomer solution [a solution of styrene (1294 g) and 2-ethylhexyl acrylate (1058 g)] and initiator solution [ammonium persulfate (9 g) dissolved in water (210 g)] are added simultaneously. The monomer solution is added over three hours while the initiator solution over four hours. The resulting polymer emulsion is cooled to ambient temperature and is approximately 46% solids. The composition of the particles is 70 parts styrene/2-ethylhexyl acrylate copolymer (55/45, molecular weight is 250,000) core and 30 parts (65/35) styrene/acrylic acid shell. The particle size of the core-shell is typically about 80 nm to about 120 nm. The glass transition temperature (Tg) is 37 C.

What is claimed:

1. An emulsion comprising an organic discontinuous phase which is distributed throughout a continuous aqueous phase, wherein the organic phase comprises
    a) C12-15 alkyl benzoate organic solvent and
    b) an addition polymer formed from 40 to 90% by weight stearyl methacrylate, 10 to 40% by weight of maleic anhydride and 30 to 50% by weight styrene as an organic phase stabilising material,
   where the emulsion further comprises an encapsulated fragrance, said fragrance is encapsulated in microparticles,
   wherein the microparticles comprise a core-shell configuration and
   wherein the shell part of the microparticle comprises a polymer formed from the combination of acrylic acid and styrene, and
   wherein the core part of the microparticle comprises a polymer formed from the combination of styrene and 2-ethylhexylacrylate.

2. An emulsion according to claim 1 wherein the amount of organic solvent is between 0.01% and 50% by weight based on the total weight of the emulsion.

3. An emulsion according to claim 1 wherein the amount of organic phase stabilising material is from about 0.01 to about 15.0% by weight based on the total weight of the emulsion.

4. An emulsion according to claim 1 wherein the amount of fragrance is from about 0.001% to about 20% by weight based on the total weight of the emulsion.

5. An emulsion according to claim 4 wherein the amount of fragrance is from about 0.01% to about 10% by weight based on the total weight of the emulsion.

6. An emulsion according to claim 5 wherein the amount of fragrance is from about 0.1% to about 1% by weight based on the total weight of the emulsion.

7. An emulsion according to claim 1 wherein the polymer formed from styrene and 2-ethylhexylacrylate of the core part of the microparticle has an average molecular weight of about 150,000 to about 350,000.

8. An emulsion according to claim 1 wherein the polymer formed from acrylic acid and styrene of the shell part of the microparticle has an average molecular weight of about 6,000 to about 15,000 g/mol.

9. A personal care composition comprising an effective amount of the emulsion according to claim 1.

10. A method of improved fragrance delivery to the human body said method comprising the steps of:
    a) applying an effective amount of a personal care composition comprising an emulsion according to claim 1 to at least one part of the human body; and
    b) rubbing the effected part of the human body with sufficient force to efficiently distribute the personal care composition evenly.

* * * * *